ately if deemed appropriate. For example, the application of a smaller amount of neutralizer solution typically gives a stronger curl or wave.

United States Patent [19]
Ballard

[11] Patent Number: 5,080,116
[45] Date of Patent: Jan. 14, 1992

[54] METHOD FOR HAIR CONDITIONING AND PERMANENTS

[76] Inventor: Gerald W. Ballard, 4798 Dierker Rd., Columbus, Ohio 43220

[21] Appl. No.: 585,748

[22] Filed: Sep. 20, 1990

[51] Int. Cl.⁵ .............................................. A45D 7/04
[52] U.S. Cl. ................................... 132/204; 132/205; 132/207; 424/71
[58] Field of Search ............... 132/200, 202, 203, 204, 132/205, 206, 207, 208; 424/71

[56] References Cited

U.S. PATENT DOCUMENTS

| | | | |
|---|---|---|---|
| 2,133,638 | 10/1938 | Singerman | 132/200 |
| 2,738,793 | 3/1956 | Voorhees | 132/207 |
| 3,907,984 | 9/1975 | Calvert et al. | 424/71 |
| 4,369,037 | 1/1983 | Matsunaga et al. | 424/71 |
| 4,373,540 | 2/1983 | de la Guardia | 132/204 |
| 4,979,524 | 12/1990 | Anderson | 132/202 |

FOREIGN PATENT DOCUMENTS 0933343  4/1948  France ................................. 132/207

*Primary Examiner*—John J. Wilson
*Assistant Examiner*—Frank A. LaViola
*Attorney, Agent, or Firm*—Biebel & French

[57] ABSTRACT

An improved method for giving a permanent comprising the steps of wrapping the hair around perm rods, applying permanent wave solution to the hair, placing the head in a heated environment, rinsing the head with water, towel drying the hair, applying neutralizer to the hair, again rinsing the head with water, and removing the rods is disclosed. The improvement comprises applying the neutralizer to the hair by an air brush with the neutralizer being applied to the hair in conjunction with a gas in a gas/neutralizer mix with the gas being at a pressure above the ambient pressure of the air. Further, the gas/neutralizer mix when applied to the hair preferably has a temperature less than the ambient temperature of the neutralizer. Preferably the neutralizer is applied to each rod more than once.

9 Claims, No Drawings

METHOD FOR HAIR CONDITIONING AND PERMANENTS

BACKGROUND OF THE INVENTION

This invention relates to conditioning of and permanents for hair, and more particularly to an improved method for conditioning hair and neutralizing permanents.

Many individuals, particularly women, find it to be desirable, if not necessary, to utilize permanents in conjunction with the styling of their hair. Typical permanent wave solutions use an alkaline solution to "soften" the hair in an attempt to conform the hair shaft to the shape of a permanent wave rod. The permanent wave solution is applied to the hair following the wrapping of the hair around perm rods. After the solution is applied, the head is typically covered with a plastic enclosure such as a bag or hair dryer which has been pre-heated to a temperature which often may exceed 100 degrees. The plastic enclosure remains on the head for about 20 minutes thereby contributing to the "softening" of the cuticle of the hair shaft. The hair is then rinsed with tepid water, approximately 90-100° F., for several minutes, typically 5 minutes and then towel dried.

At this point in the process, an acidic solution which is known as neutralizer is applied through the use of a plastic squeeze bottle. The neutralizer is usually at room temperature and is allowed to remain on the hair shaft for several, typically 5, minutes. The rods are then rinsed again with water, and then removed. The neutralizer returns the hair to its original acid state, such that it then can be styled.

Since most prior art permanents last for only a couple of months, often in the range of 3-4, this process must be repeated several times a year. Over the course of time, the acidic neutralizer solution tends to burn the hair, due to the amount which is applied to neutralize the alkaline solution already on the hair. Additionally, the application of the neutralizing solution through the use of a plastic squeeze bottle tends to result in the solution running down the neck and face of the individual. For this reason, towels are placed on the neck and cotton is used around the hair line to prevent the acidic solution from damaging sensitive body parts, such as the eyes.

Thus, the need exists for an improved method of giving permanents which results in a longer lasting hold, with deeper penetration of the neutralizing solution, while at the same time utilizing less neutralizer.

SUMMARY OF THE INVENTION

This invention relates to an improved method for giving a permanent to hair with the improvement comprising the application of neutralizer to the hair by means of an air brush, with the neutralizer being applied to the hair in conjunction with a gas in a gas/neutralizer mix, with the gas being at a pressure above the ambient mix. Preferably the gas is also at a pressure above the ambient pressure of the air.

The preferable method of practicing the invention involves having the neutralizer being applied to one perm rod at a time using short strokes, with the air brush being held between 0.1-1.0" from the hair during the application of the neutralizer. More than one application of neutralizer may be made to the hair. If more than one application of neutralizer is used, preferably at least one of the applications of neutralizers is made with the gas pressure being greater than 40 lbs. The gas which is preferably utilized is carbon dioxide.

This invention also relates to an improved method for conditioning the hair, with the improvement comprising the application of neutralizer to the hair by means of an air brush, with the neutralizer being applied to the hair in conjunction with a gas in a gas/neutralizer mix. Preferably the gas is applied at a pressure above the ambient pressure of the air.

Accordingly, it is an object of this invention to provide an improved method for giving a permanent which results in a longer lasting hold than is currently possible using existing methods of permanents.

It is another object of this invention to provide an improved method for giving a permanent whereby results as good as those obtainable through prior methods can be obtained but through the utilization of less neutralizer.

It is another object of this invention to provide an improved method for giving a permanent which results in extremely manageable hair when the results of a permanent utilizing the method of this invention are compared with the results of prior art permanents.

It is still another object of this invention to provide an improved method for giving a permanent, such than utilization of an acid wave solution will bring results as good as that of an alkaline wave solution.

It is another object of this invention to provide an improved method for the conditioning of hair.

Other objects and advantages of the invention will be apparent from the following description and the appended claims.

DESCRIPTION OF THE PREFERRED EMBODIMENT

The invention discloses an improved method for giving a permanent. The typical permanent comprises the steps of wrapping the hair around perm rods; applying permanent wave solution to the hair; placing the head in a heated environment; rinsing the head with water; towel drying the hair; applying neutralizer to the hair; again rinsing the head with water; and then removing the rods. These steps are performed sequentially. As opposed to the prior art method of applying the neutralizer full-strength to the hair by using a plastic squeeze bottle, this invention discloses an improvement in the method for applying the neutralizer with that improvement comprising applying the neutralizer by means of an air brush. The type of air brush used is the type often used by artists.

A representative air brush capable of use in the method of this invention is made by the Binks Manufacturing Company of Franklin Park, Ill. The brush includes a square, chrome-plated trigger button with single-action control to monitor the flow of gas. The brush also includes a small, knurled screw which can be used to limit the movement of the trigger button and consequently the flow of gas.

The air brush has an air intake which can be connected to a compressor or other source of gas in the known manner. The gas utilized with the air brush could be the air of the atmosphere, but preferably is a specific gas such as carbon dioxide or nitrogen. In any event, the gas is kept under pressure. Preferably the pressure is of at least 40 pounds and more preferably is between 70-80 pounds, such that the gas is at a pressure above the ambient pressure of the air. The air brush also includes a bottle assembly which in normal artistic applications is used to hold pigment or other fluid, but in this particular method the bottle is used to hold neutralizer, and may utilize the plastic bottle normally used to disperse neutralizer.

Using this particular inventive method permits the utilization of less than 2 ounces of neutralizer in order to effect the neutralization of the permanent wave solution on a treated head, contrasted to the normal amounts associated with permanent neutralizations, which often range about 4 ounces.

The utilization of the improved method of this invention preferably results in the neutralizer being applied to the hair as a spray in conjunction with a gas in a gas/neutralizer mix. Preferably the mix is at least 50% gas with 50% neutralizer, such that the ratio in the mixture of gas to neutralizer is at least 1:1. However, it has been found that acceptable results can be reached with an even greater proportion of gas to neutralizer present. Also, the gas/neutralizer when applied to the hair is of a temperature less than the ambient temperature of the neutralizer.

Preferably the method of this invention includes applying the neutralizer to one rod at a time with short bursts of the gas/neutralizer mixture using relatively short strokes. After the entire head has neutralizer applied to each curl one at a time, each curl is preferably sprayed at least one more time. More preferably, especially with longer hair or hair which is very dry or tinted, three applications are administered, in amounts of between ½ to ¾ ounces of neutralizer per application.

To assist the mixture in thoroughly neutralizing the permanent wave solution with a minimal amount of mess, the air brush is preferably held with the index finger operating the trigger button and with the air hose (if any) passing below the thumb and over the wrist to keep the hose out of the way. Additionally, the air brush is held between 0.1 and 1.0" from the hair during the application process.

Utilization of this improved method has resulted in the ability to completely neutralize permanent wave solution with approximately ½ to 2 ounces of neutralizer, where formerly approximately 4 ounces were necessary. Furthermore, there is a marked decrease in messiness, even when each curl is sprayed three times. Additionally, the cuticle layer of the hair lays closer to the shaft relative to prior art permanents, or application of neutralizer. In fact, it is believed that as long as the perm remains in the hair, the cuticle will remain essentially flat relative to the shaft.

It has been found that when each curl is sprayed three times, either of two techniques work extremely well. In the first technique, the rod is lifted and the bottom of the curl is sprayed, then the curl is partially restored to its original position and sprayed again, and then the curl is sprayed a third time with the rod in its original position, with the third spraying being along the top of the curl. Another technique which has also produced excellent results has the first application being made to the top of the curl, the second application being made to the bottom of the curl, and the third application being again being made intermediate the top and bottom of the curl.

It has also unexpectedly been found that the method of applying neutralizer to the hair by means of an air brush with the neutralizer being applied to the hair in conjunction with a gas in a gas/neutralizer mix produces unexpected results in providing an improved method in the conditioning of hair. This improved method also comprises the steps of rinsing the head with water, towel drying the hair, and again rinsing the head with water following the application of neutralizer to the hair.

Applying the neutralizer by means of an air brush even when there is no permanent wave solution present, results in better feeling and better looking hair. This improved method for conditioning the hair involves the same equipment and technique as discussed above when the neutralizer is applied to the hair in conjunction with a permanent.

The invention will be better understood in view of the following examples, which are illustrative only and should not be construed as limiting the invention.

EXAMPLE 1

Subject A was 68 years old and had fine, gray hair. Relaxation of permanents applied using the prior art method occurred in two weeks. Subject A had permanent wave solution applied and her hair covered with a plastic bag. The covered head was placed for twenty minutes in a dryer pre-heated to 115° F. After the twenty minutes, the temperature under the plastic bag was 91° F. The hair was uncovered and then rinsed for five minutes. The hair then had neutralizer applied using the method of the invention. The neutralizer was rinsed off after five minutes. In follow-up the perm did not relax for at least two months, which was roughly four times the normal period.

EXAMPLE 2

Subject B was 50 years old and had relatively short hair. The subject was given a permanent using the improved method. Several months later she was given one using the prior art method. On a subsequent occasion for getting a permanent, she was given the option of choosing the method of permanent to be given. She chose the method of the invention, citing the way her hair looked and the longer length of time before her hair relaxed.

EXAMPLE 3

Subject C was 60 years old and had very fine and dry, color-treated hair. The subject was given a permanent using the improved method. Following prior perms which used the prior art method, her hair did not respond favorably to attempts to style it so as to give it the appearance of fullness or body. After the perm of this Example, the manageability of her hair was such that it permitted such styling with favorable results, with such styling being able to last instead of quickly losing the perm.

EXAMPLE 4

Subject D was 9 years old and had waist length hair. The neutralizer was applied to the hair in a mixture of 50% neutralizer and 50% $CO_2$ (carbon dioxide) under 90 pounds of pressure. After more than four months, the subject's hair still exhibited curl.

EXAMPLE 5

Subject E was given a permanent using an acid wave solution and the improved method. Over the next several weeks, the hair stayed firm throughout, and looked as good as if an alkaline wave had been used. Approximately five months after the above perm, the subject was given another perm, but utilizing the conventional method of neutralizing. The hair as a whole relaxed quicker than with the perm using the invention. After one month the crown area had noticeably relaxed relative to near the scalp. Overall, the manageability of the hair wa not as good.

EXAMPLE 6

Subject F was 68 years old and had fine hair whose curl relaxed so quickly after permanents that she had received subsequent perms within two months. She was given a perm using the method of this invention. The neutralizer was applied to the hair in a mixture of 50% neutralizer and 50% $CO_2$ under 70 pounds of pressure. The hair was examined weekly for the next three months, over which time it exhibited very little relaxation.

EXAMPLE 7

Subject E was given another permanent. When it was time to apply the neutralizer, the application was done in a series of three applications; first over, then under, then over the curling rods. The mix was mostly air, such that less neutralizer was used for all three applications, than in two applications where the neutralizer/gas ratio is 1:1. Also, following the third application, instead of permitting the hair to set for five minutes before removing the rods, the rods were removed immediately. The hair exhibited good lasting curl.

It may be appreciated that the method of this invention results in permanents exhibiting strong, long lasting hold while using less neutralizer than has been taught and used in the prior art of the giving of permanents. This method results in less mess, more manageable hair in certain instances, and a longer lasting hold. For example, in at least one case a permanent given using the method of this invention lasted 1 year.

Additionally, the reduced amount of neutralizer necessary when practicing the method of this invention is believed to reduce the extent of chemical burning which occurs to the hair since only a fraction of the amount of neutralizer previously used is now necessary.

While the method herein described constitutes a preferred embodiment of this invention, it is to be understood that the invention is not limited to this precise method and that changes may be made therein without departing from the scope of the invention, which is defined in the appended claims.

What is claimed is:

1. An improved method for giving a permanent comprising the steps of
   1) wrapping hair around perm rods,
   2) applying permanent wave solution to the hair,
   3) rinsing the head with water,
   4) towel drying the hair,
   5) applying neutralizer to the hair,
   6) again rinsing the head with water, and
   7) removing the rods, the improvement comprising the method for applying said neutralizer to said hair, said improvement comprising applying said neutralizer by means of an air brush to mix with a gas, said neutralizer being applied to the hair by lifting rods, spraying the bottom of the hair wrapped around the perm rod, partially restoring the hair wrapped around the perm rod to its original position and then spraying the hair wrapped around the rod again, and finally spraying the hair wrapped around the perm rod a third time with the rod in its original position, the air brush being held between 0.1-1.0 inches from the hair while the neutralizer is being applied, and wherein at least one application of neutralizer is made with a gas pressure of greater than 40 lbs.

2. The method according to claim 1 wherein at least one application of neutralizer is made with the gas pressure being between 70 and 80 lbs.

3. The method according to claim 1 wherein said gas/neutralizer mix when applied to the hair has a temperature less than the ambient temperature of the neutralizer.

4. The method according to claim 1 wherein said gas is carbon dioxide.

5. An improved method for giving a permanent comprising the steps of
   1) wrapping hair around perm rods,
   2) applying permanent wave solution to the hair,
   3) rinsing the head with water,
   4) towel drying the hair,
   5) applying neutralizer to the hair,
   6) again rinsing the head with water, and
   7) removing the rods, the improvement comprising the method for applying said neutralizer to said hair, said improvement comprising applying said neutralizer by means of an air brush to mix with a gas, said neutralizer being applied to the hair by lifting rods, spraying the bottom of the hair wrapped around the perm rod, partially restoring the hair wrapped around the perm rod to its original position and then spraying the hair wrapped around the rod again, and finally spraying the hair wrapped around the perm rod a third time with the rod in its original position, the air brush being held between 0.1-1.0 inches from the hair while the neutralizer is being applied and wherein at least one application of neutralizer is made with a gas pressure of greater than 40 lbs, said gas being carbon dioxide, and said gas/neutralizer mix when applied to the hair having a temperature less than the ambient temperature of the neutralizer.

6. An improved method for giving a permanent comprising the steps of
   1) wrapping hair around perm rods,
   2) applying permanent wave solution to the hair,
   3) rinsing the head with water,
   4) towel drying the hair,
   5) applying neutralizer to the hair,
   6) again rinsing the head with water, and
   7) removing the rods, the improvement comprising the method for applying said neutralizer to said hair, said improvement comprising applying said neutralizer by means of an air brush to mix with a gas, said neutralizer being applied to the hair by spraying the top of the curl, then spraying the bottom of the curl, and the spraying the curl intermediate the top and the bottom of the curl, the air brush being held between 0.1-1.0 inches from the hair while the neutralizer is being applied, and wherein at least one application of neutralizer is made with a gas pressure of greater than 40 lbs.

7. The method according to claim 6 wherein at least one application of neutralizer is made with the gas pressure being between 70 and 80 lbs.

8. The method according to claim 6 wherein said gas/neutralizer mix when applied to the hair has a temperature less than the ambient temperature of the neutralizer.

9. The method according to claim 6 wherein said gas is carbon dioxide.

* * * * *